United States Patent
Comiter et al.

(10) Patent No.: US 11,992,630 B2
(45) Date of Patent: May 28, 2024

(54) DEVICES FOR ASSISTING SELF-CATHETERIZATION AND METHODS FOR USING SUCH DEVICES

(71) Applicant: THE BOARD OF TRUSTEES OF THE LELAND STANFORD JUNIOR UNIVERSITY, Stanford, CA (US)

(72) Inventors: Craig Comiter, Palo Alto, CA (US); Gabe Ho, Detroit, MI (US); Maria Iglesias, Scottsdale, AZ (US); Isaac Justice, Dresden (DE); Amanda Urke, Medina, MN (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 634 days.

(21) Appl. No.: 17/001,569

(22) Filed: Aug. 24, 2020

(65) Prior Publication Data

US 2021/0052852 A1    Feb. 25, 2021

Related U.S. Application Data

(60) Provisional application No. 62/894,631, filed on Aug. 30, 2019, provisional application No. 62/891,343, filed on Aug. 24, 2019.

(51) Int. Cl.
*A61M 25/01*    (2006.01)
*A61M 25/00*    (2006.01)

(52) U.S. Cl.
CPC .... *A61M 25/0116* (2013.01); *A61M 25/0017* (2013.01); *A61M 25/01* (2013.01); *A61M 2210/1085* (2013.01); *A61M 2210/1089* (2013.01)

(58) Field of Classification Search
CPC .......... A61M 25/01; A61M 2210/1089; A61F 5/4553; A61F 5/44; A61F 25/01
See application file for complete search history.

(56) References Cited

U.S. PATENT DOCUMENTS

| | | | | |
|---|---|---|---|---|
| 5,045,078 A | * | 9/1991 | Asta | A61M 25/01 600/574 |
| 5,084,036 A | * | 1/1992 | Rosenbaum | A61M 25/01 604/329 |
| 8,998,883 B1 | * | 4/2015 | Feloney | A61M 25/0041 604/93.01 |
| 9,108,020 B1 | * | 8/2015 | Feloney | A61M 25/0043 |

(Continued)

*Primary Examiner* — Benjamin J Klein
*Assistant Examiner* — Meagan Ngo
(74) *Attorney, Agent, or Firm* — William A. English; VISTA IP LAW GROUP LLP

(57) ABSTRACT

Devices and methods are provided to facilitate self-catheterization of a urethra. In an exemplary embodiment, the device includes an elongate anchor member comprising a proximal end and a rounded distal end to facilitate insertion into a user's vagina, a bridge extending laterally from an intermediate location of the anchor member, a guide on the bridge spaced apart from the anchor member such that the guide is aligned with the user's urethra, the guide including a passage therethrough sized to receive a urinary catheter therethrough, and a handle on the proximal end of the anchor member to facilitate manipulation by the user and consistent, accurate alignment of the guide.

18 Claims, 10 Drawing Sheets

(56) References Cited

U.S. PATENT DOCUMENTS

| | | | |
|---|---|---|---|
| 2010/0204666 A1* | 8/2010 | Feloney | A61M 25/01 604/347 |
| 2010/0256580 A1* | 10/2010 | Faber | A61M 25/0017 604/329 |
| 2015/0238732 A1* | 8/2015 | Ritmiller | A61M 25/01 604/544 |
| 2017/0202692 A1* | 7/2017 | Laniado | A61F 5/4553 |
| 2018/0008804 A1* | 1/2018 | Laniado | A61M 25/01 |

\* cited by examiner

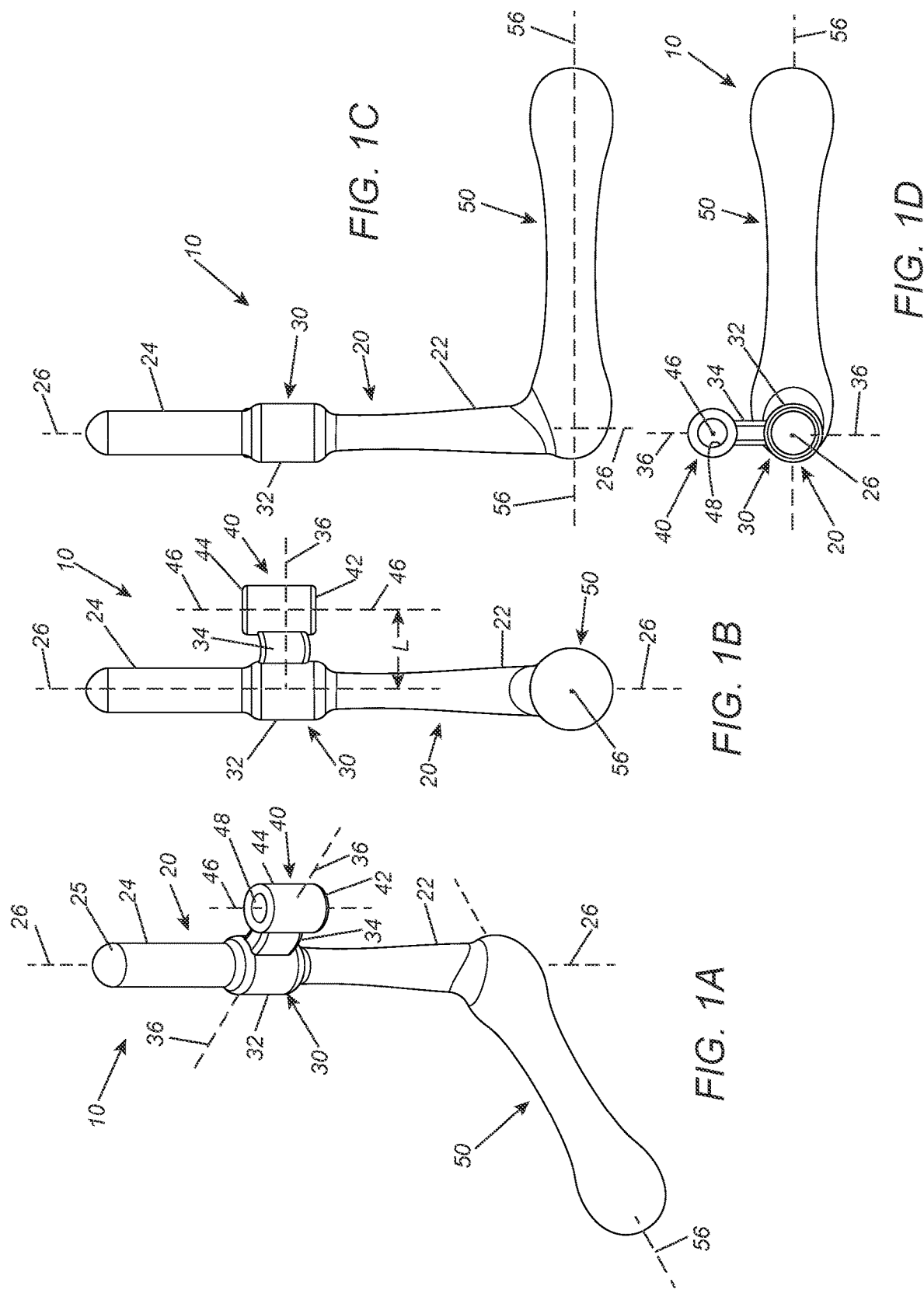

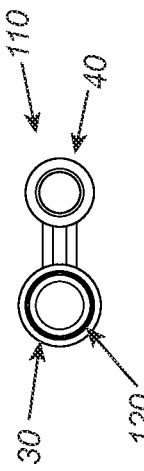
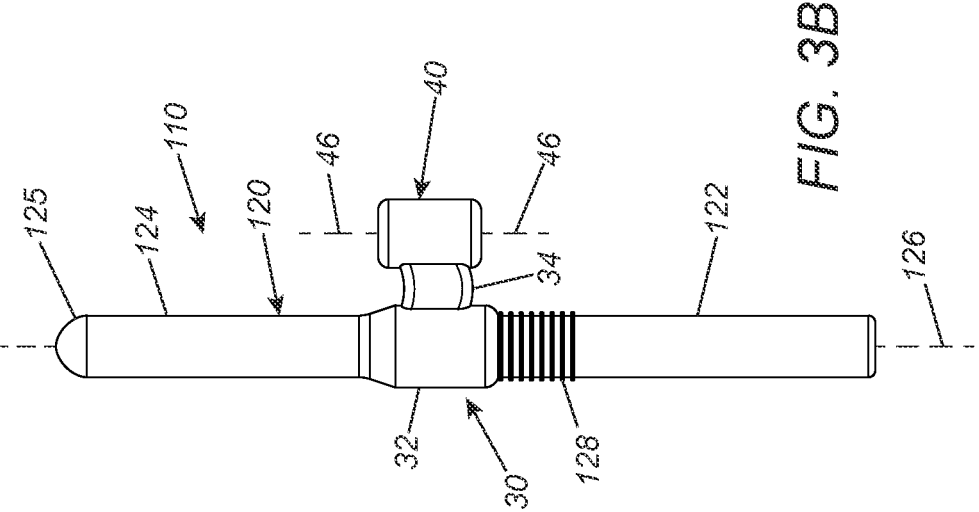
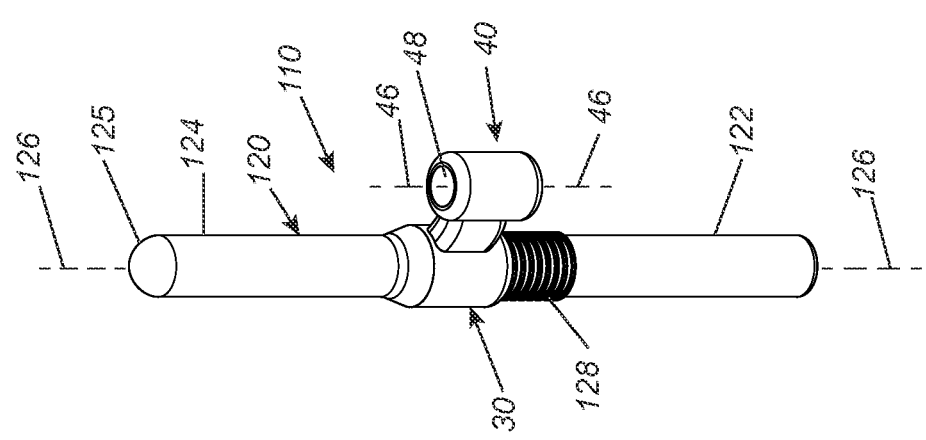
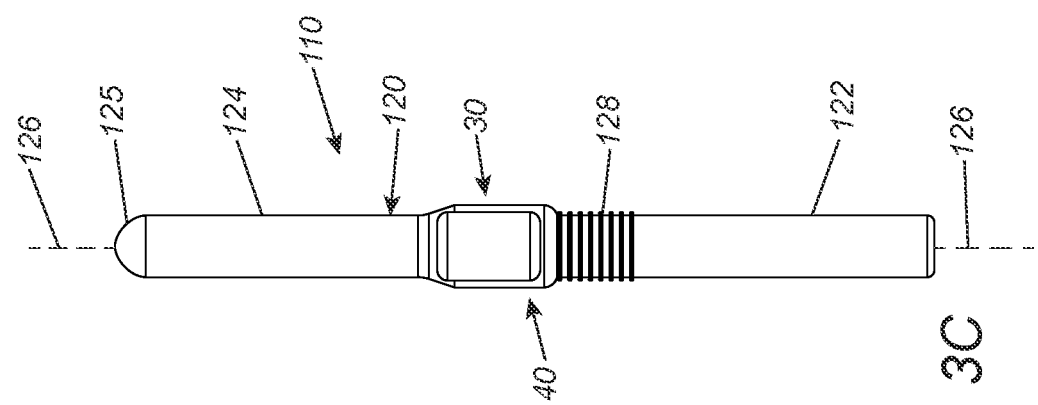

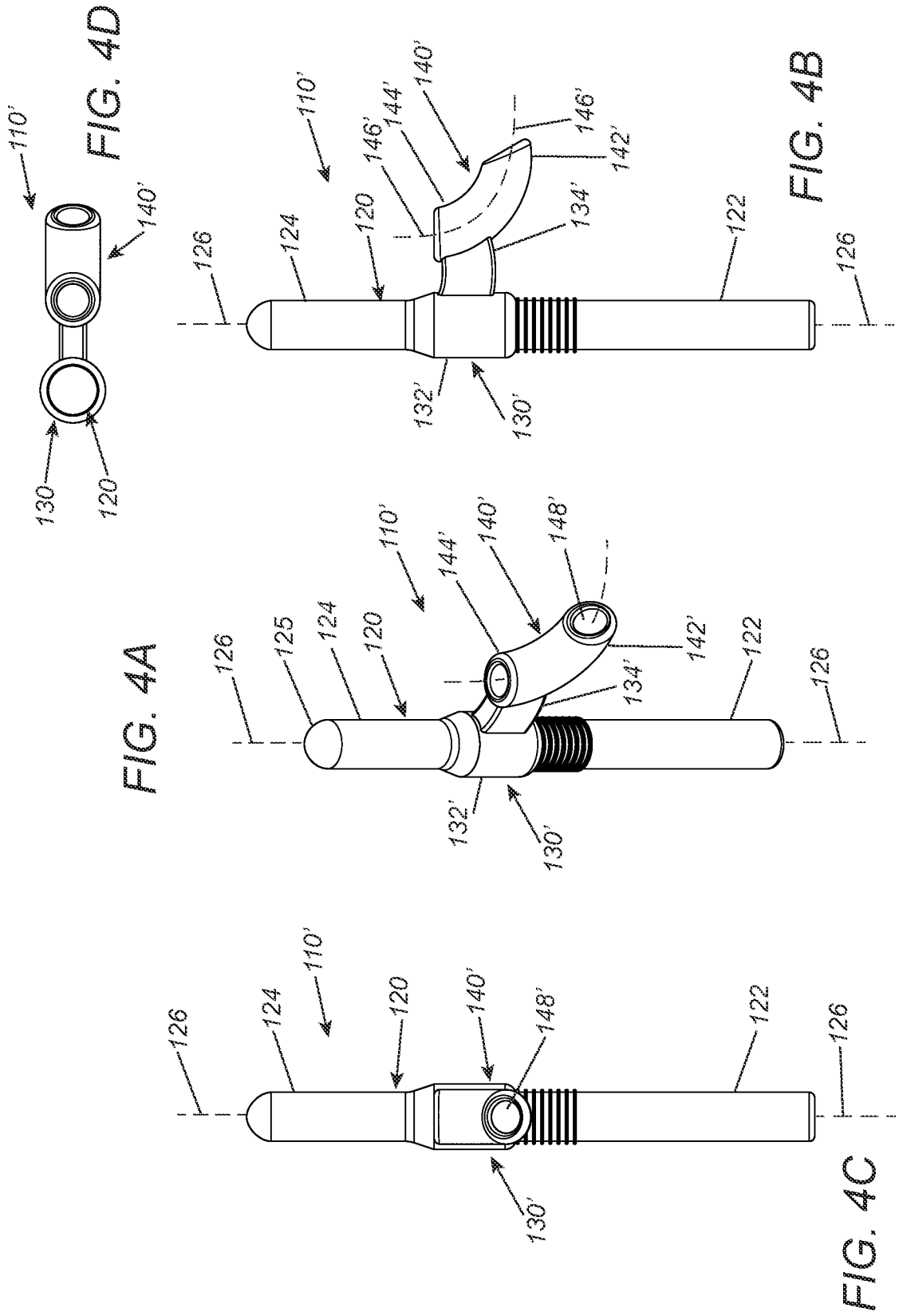

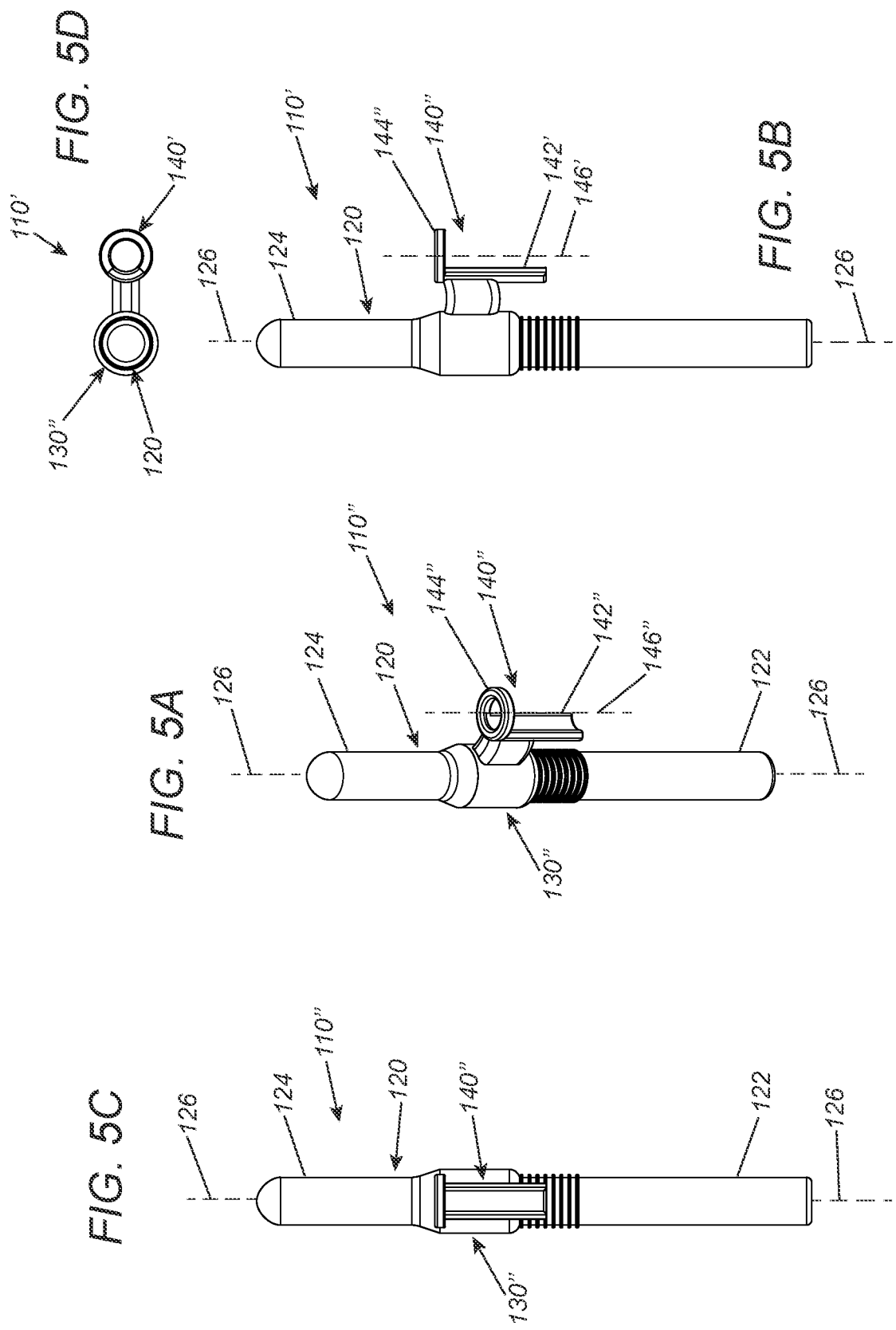

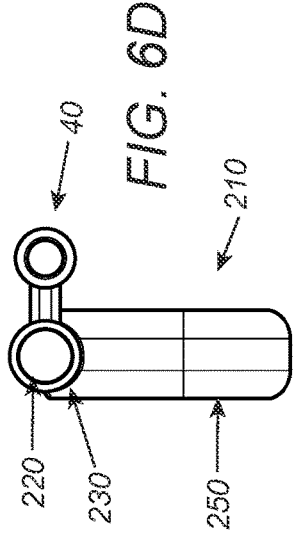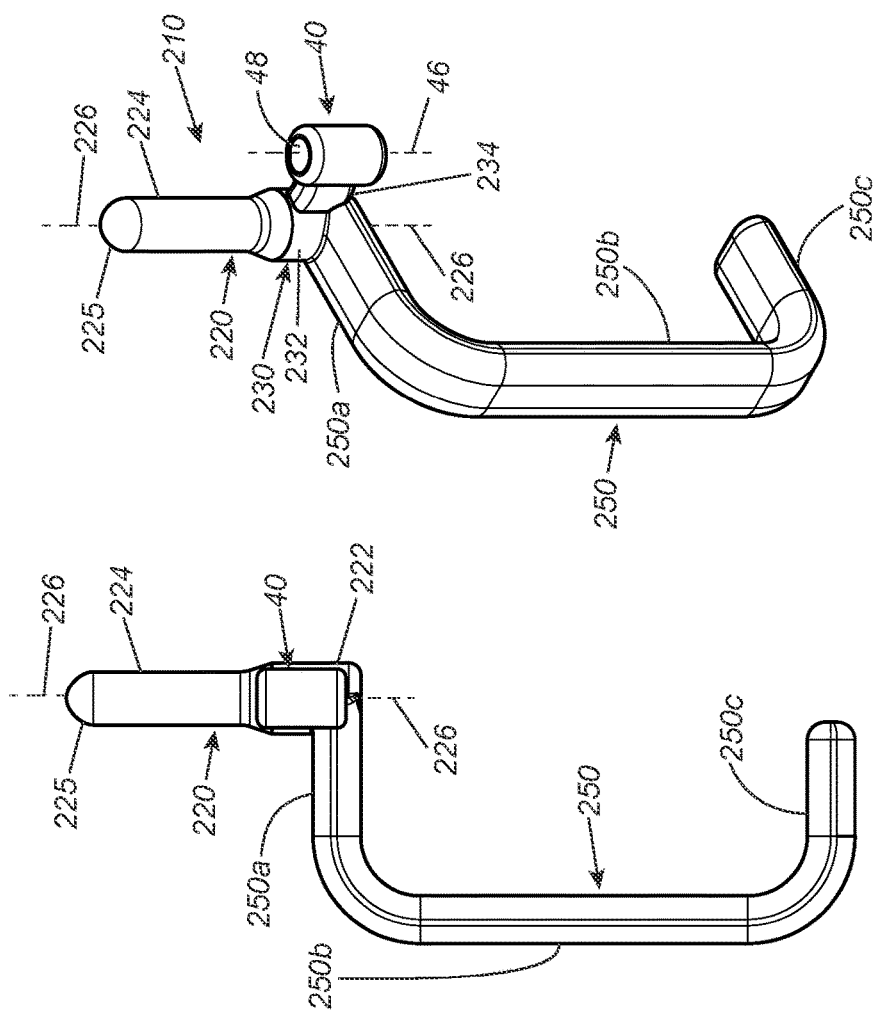

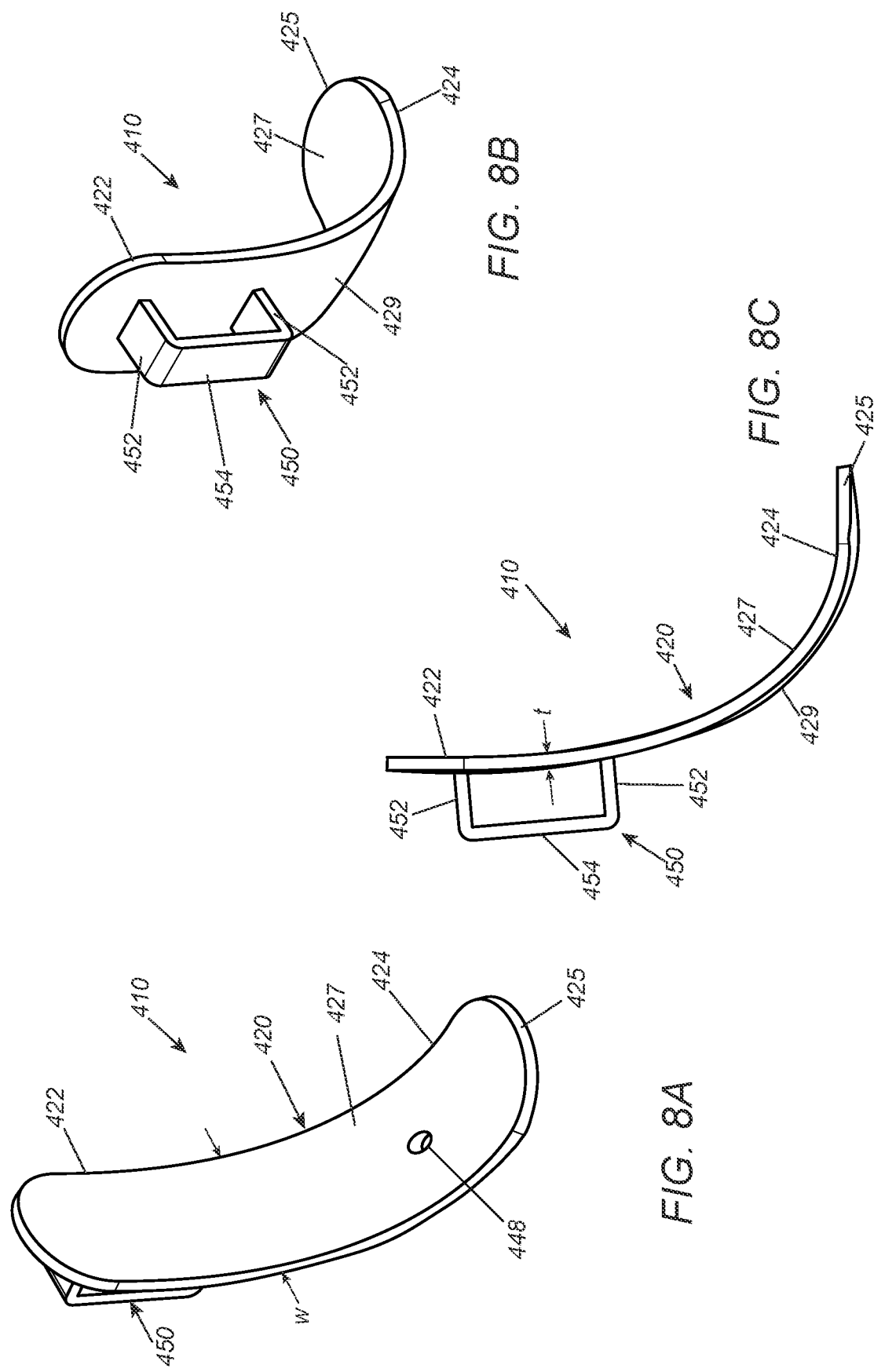

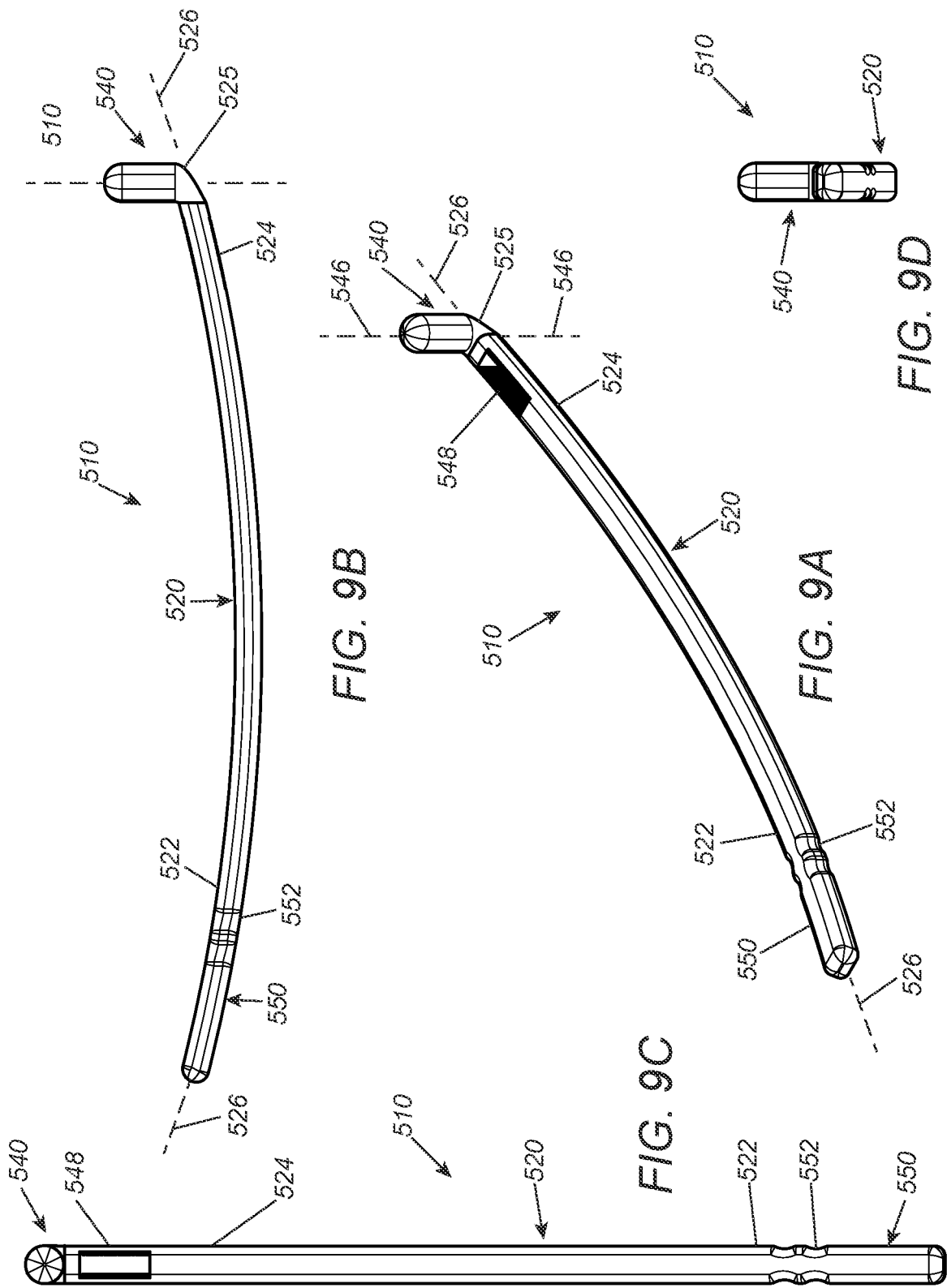

DEVICES FOR ASSISTING SELF-CATHETERIZATION AND METHODS FOR USING SUCH DEVICES

RELATED APPLICATION DATA

The present application claims benefit of U.S. provisional application Ser. No. 62/891,343, filed Aug. 24, 2019 and 62/894,631, filed Aug. 30, 2019, the entire disclosures of which are expressly incorporated by reference herein.

FIELD OF THE INVENTION

The present invention relates to medical devices, and, more particularly, to devices for assisting with self-catheterization and to methods for using such devices.

BACKGROUND

Over 250,000 women in the U.S. suffer from neurogenic bladder ("NB"), or bladder dysfunction caused by neurological damage. NB can result in overflow incontinence, where the bladder does not contract and one never feels the urge to urinate. This inability to void manifests itself as a constant leaking when the bladder is full, resulting in social embarrassment and urinary tract infections ("UTIs") from stagnant urine. The standard of care for NB is clean intermittent catheterization ("CIC"), where a patient inserts a single-use catheter up the urethra to void their bladder 4-6 times a day. However, CIC for females is difficult to perform, in part due to the challenge of locating the urethra, and results in an average of 2.5 UTIs per patient per year and up to five times higher than the rate of UTIs in women free of chronic disease.

Literature suggests two mechanisms by which CIC increases UTI risk. First, the female urethra is obscured by the labia minora, making females likely to miss the urethra and contaminate the catheter tip with periurethral bacteria. Second, this difficulty in locating the urethra contributes to the challenge of voiding the recommended number of times per day. Infrequent catheterization increases the amount of stagnant urine in the bladder at any given time, increasing the risk of UTIs. Studies have found a five-fold decrease in UTIs when catheterization occurred six times a day compared to three times a day.

One device designed to assist women in self-catheterization by helping locate the urethra is the Asta-Cath catheter guide. However, since the Asta-Cath was discontinued, there are currently no catheterization assistive devices in production. Instead, improvements to catheters themselves have been proposed, such as the SpeediCath® from Coloplast A/S Corporation. While compact and more comfortable to insert, the SpeediCath® leaves the difficulty of locating the urethra and other infection risk factors unmitigated. Visually confirming the location of the urethra before inserting such catheters may be difficult, requiring users to strap mirrors to their leg or try to hold a mirror to identify the proper location of the urethra before insertion, further complicating self-catheterization.

Accordingly, devices and methods to assist with self-catheterization and address the gap in existing technologies would be useful.

SUMMARY

The present invention is directed to medical devices, and, more particularly, to devices for assisting with self-catheterization and to methods for using such devices.

In accordance with an exemplary embodiment, a device is provided to assist with self-catheterization that aims to improve female proficiency of clean intermittent catheterization by helping females locate and guide a catheter into the urethra without caregiver or physician assistance. By preventing failed catheterization attempts, the device may decrease catheter contamination with periurethral bacteria. Further, by making the process easier, the device may allow patients to catheterize more frequently, reducing the amount of stagnant urine in the bladder. Ultimately, these improvements may reduce the risk of UTIs beyond that of the current standard of care.

The device's design may allow patients to more easily find their urethra during self-catheterization by anchoring the device relative to a well-known anatomical landmark near the urethra, such as inside the vagina. After anchoring, the device uses a bridge and guide that matches the distance between the vagina and urethra to assist in the accurate and/or efficient placement of a catheter into the urethra.

In accordance with an exemplary embodiment, a device is provided that includes an elongate anchor member including a proximal portion and a distal portion sized and/or shaped to facilitate insertion into a user's vagina; a bridge extending laterally from an intermediate location of the anchor member; a guide on the bridge spaced apart from the anchor member such that the guide is aligned with the user's urethra, the guide including a passage therethrough sized to receive a urinary catheter therethrough; and a handle on the proximal end of the anchor member to facilitate manipulation by the user.

In accordance with another exemplary embodiment, a method is provided for self-catheterization using a guide device that includes the following steps: 1) a user anchors the device by inserting a vaginal insert or anchor member into the user's vagina, e.g., similar to the mechanism for inserting a tampon, or otherwise anchoring the device using well-known anatomical landmarks; 2) the user inserts a catheter into the urethra and bladder using a catheter guide on the device, which is located just below the urethra when the anchor member is properly inserted; 3) the user voids their bladder and then removes the catheter from the bladder; and 4) the user removes the anchor member from the vagina.

In accordance with yet another embodiment, a method is provided for self-catheterization by a user that includes providing an elongate anchor member comprising a proximal portion, a distal portion terminating in a distal tip, and a passage through the distal portion spaced apart from the distal tip; engaging the distal portion of the anchor member adjacent a known anatomical structure to align the passage with the user's urethra; inserting a urinary catheter through the passage into the urethra; advancing the catheter into the user's bladder; voiding urine from the bladder; and removing the catheter and anchor member.

In accordance with still another embodiment, a device is provided for facilitating self-catheterization of a urethra of a user that includes an elongate anchor member comprising a proximal portion, a distal portion sized for insertion into the user's vagina, and a longitudinal axis extending between the proximal and distal ends; a bridge extending from an intermediate location of the anchor member along a bridge axis extending laterally relative to the longitudinal axis; a guide on the bridge spaced apart laterally from the anchor member, the guide comprising a passage therethrough sized to receive a urinary catheter therethrough; and a handle extending laterally from the proximal portion of the anchor member along a handle axis extending laterally relative to the longitudinal axis, the handle axis offset radially relative to the bridge axis.

In accordance with another embodiment, a device is provided for facilitating self-catheterization of a urethra that includes an elongate anchor member comprising a proximal portion including a handle, a distal portion comprising a concave contact surface and terminating in a distal tip, and a passage through the distal portion spaced apart from the distal tip to position the passage adjacent a user's urethra when the distal tip is engaged with the user's pelvic bone, the passage sized to receive a urinary catheter therethrough.

In accordance with still another embodiment, a method is provided for self-catheterization by a user that includes providing an elongate anchor member comprising a proximal portion, a distal portion comprising a concave contact surface and terminating in a distal tip, and a passage through the distal portion spaced apart from the distal tip; positioning the distal portion of the anchor member adjacent a pelvic bone area of the user; engaging the contact surface against the pelvic bone area to align the passage with the user's urethra; inserting a urinary catheter through the passage into the urethra; advancing the catheter into the user's bladder; voiding urine from the bladder; and removing the catheter and anchor member.

In accordance with another embodiment, a device is provided to facilitate self-catheterization of a urethra that includes an elongate member comprising a proximal portion including a handle and a distal portion terminating in a distal tip; a guide member extending laterally from the distal portion adjacent the distal tip; and a passage through the distal portion spaced apart from the guide member to position the passage adjacent a user's urethra when the guide member is inserted into the user's vagina, the passage sized to receive a urinary catheter therethrough.

In accordance with yet another embodiment, a method is provided for self-catheterization by a user that includes providing an elongate anchor member comprising a proximal portion, a distal portion, and a guide member extending laterally from the distal portion, and a passage through the distal portion spaced apart from the guide member; inserting the guide member into the user's vagina to align the passage with the user's urethra; inserting a urinary catheter through the passage into the urethra; advancing the catheter into the user's bladder; voiding urine from the bladder; and removing the catheter and anchor member. Optionally, one or more additional elements on the distal portion may be engaged and/or aligned with other anatomical landmarks of the user's body to facilitate positioning the passage adjacent the urethra.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It is emphasized that, according to common practice, the various features and design elements of the drawings are not to-scale. On the contrary, the dimensions of the various features and design elements are arbitrarily expanded or reduced for clarity. Included in the drawings are the following figures:

FIGS. 1A-1D are perspective, side, and end views of an exemplary embodiment of a guide device to facilitate self-catheterization of a urethra including a tubular guide and a lateral handle.

FIGS. 3A-3D are perspective, side, and end views of another embodiment of a guide device to facilitate self-catheterization of a urethra including a tubular guide.

FIGS. 4A-4D are perspective, side, and end views of yet another embodiment of a guide device to facilitate self-catheterization of a urethra including a curved tubular guide.

FIGS. 5A-5D are perspective, side, and end views of still another embodiment of a guide device to facilitate self-catheterization of a urethra including a ring guide.

FIGS. 6A-6D are perspective, side, and end views of yet another embodiment of a guide device to facilitate self-catheterization of a urethra including a tubular guide and a hilt handle.

FIGS. 8A-8C are perspective and side views of yet another embodiment of a guide device.

FIGS. 9A-9D are perspective, side, and end views of still another embodiment of a guide device.

DETAILED DESCRIPTION OF THE EXEMPLARY EMBODIMENTS

Figure 2A:
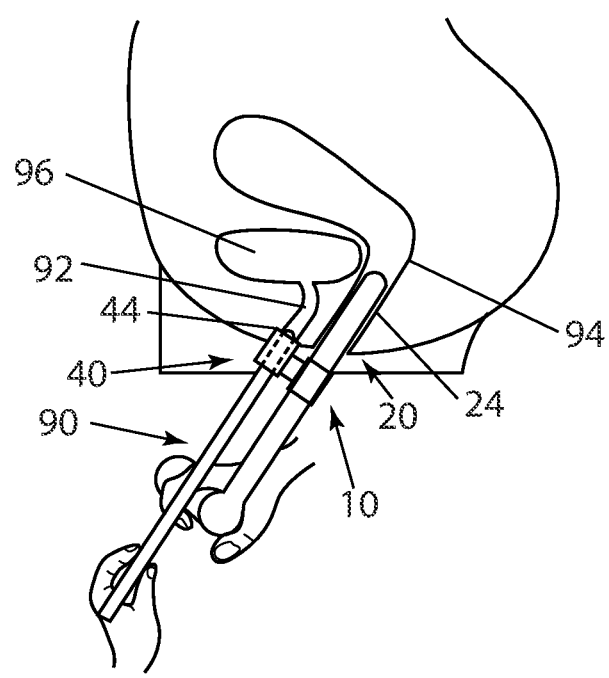
FIGS. 2A and 2B are details of a female user's pelvic region showing an exemplary method for using the guide device of FIGS. 1A-1D.

Before the exemplary embodiments are described, it is to be understood that the invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

Generally, the devices herein may improve efficiency of female self-catheterization by utilizing anatomical landmarks to aid accurate catheter placement within the urethra. The devices and methods herein may mitigate one or more UTI risk factors, such as bacterial contamination from missing the urethra and/or inadequate frequency of voiding. Importantly, the devices herein may be designed to be easily and reliably used by individuals at home without the need of physician or caregiver assistance.

One or more of the following advantages may be provided by the devices herein. First, the devices herein may improve efficiency of female self-catheterization because the device includes a guide member designed to mimic a tampon, a device many women are familiar with, to make insertion more intuitive and comfortable. Second, optionally, a personalized distance between the guide member and a catheter guide may increase the accuracy in locating the urethra. Finally, the devices herein may eliminate the need for visibility to identify where the catheter is inserted, but rather feature a mechanism of use that consistently and accurately aligns the guide member with the urethra without use of a mirror.

Figure 2B:
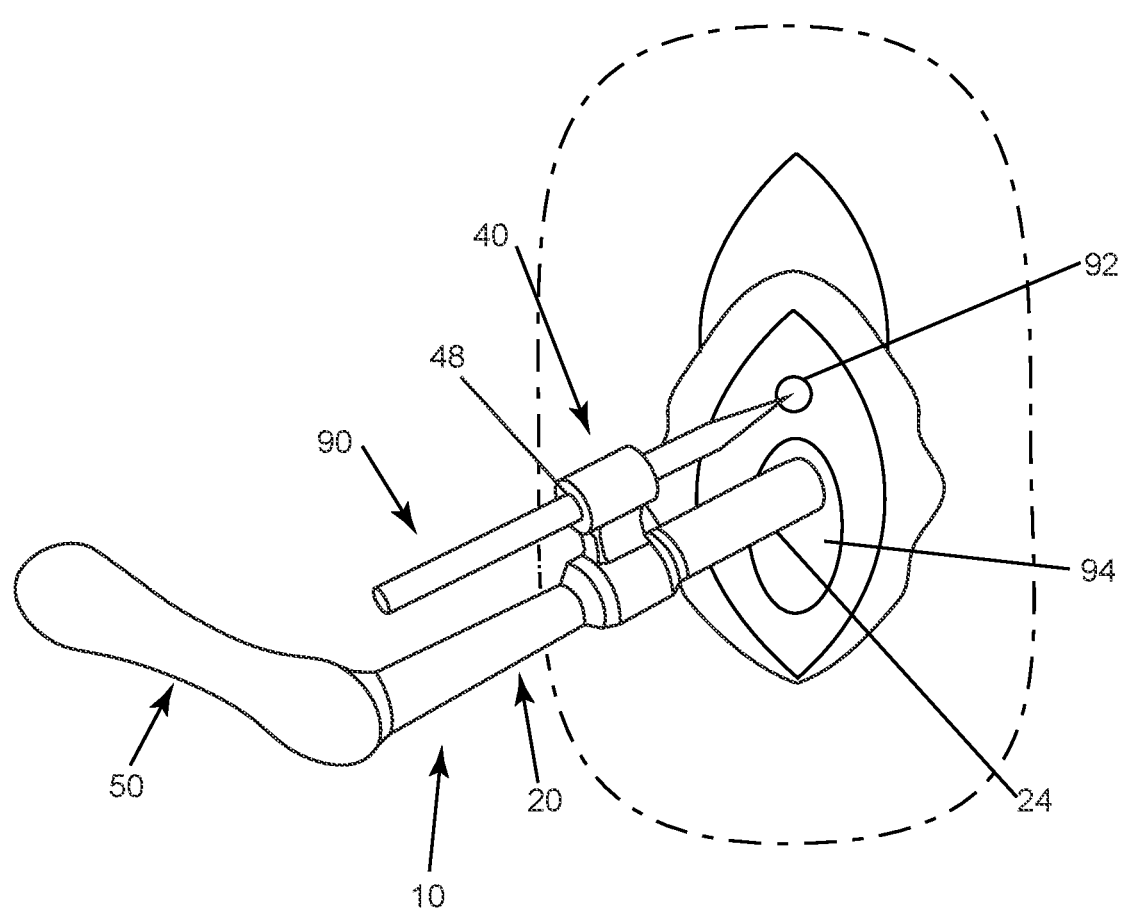
Figure 7B:
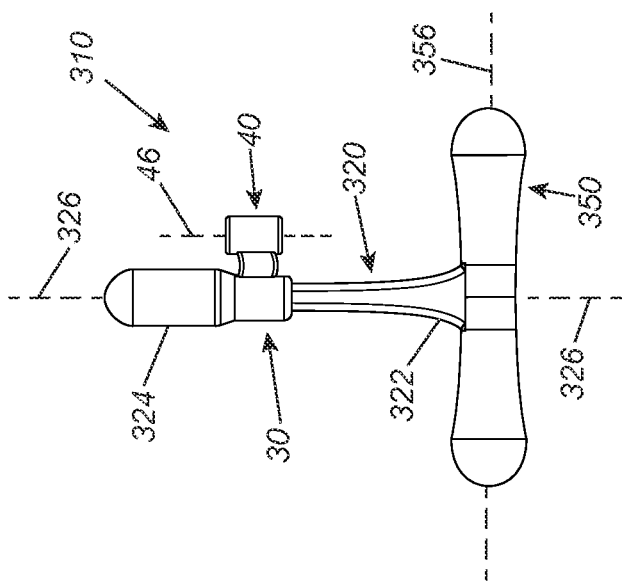
FIGS. 7A-7D are perspective, side, and end views of still another embodiment of a guide device to facilitate self-catheterization of a urethra including a tubular guide and a "T" shaped handle.
Figure 7A:
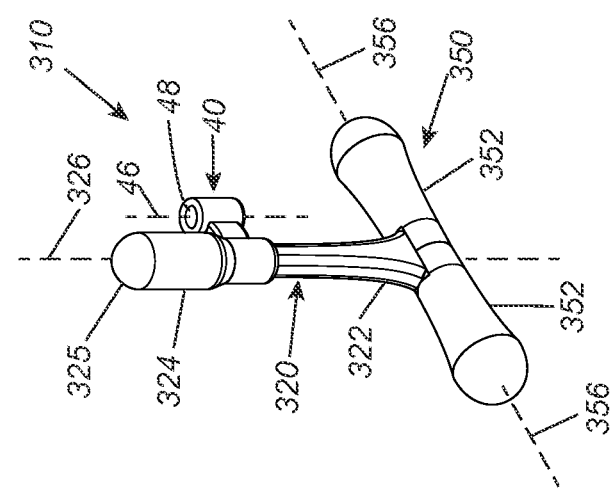
Figure 7D:
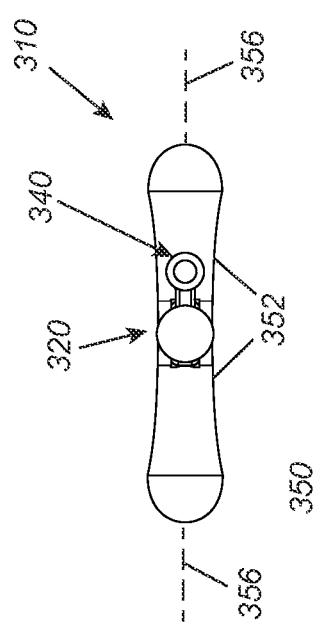
Figure 7C:
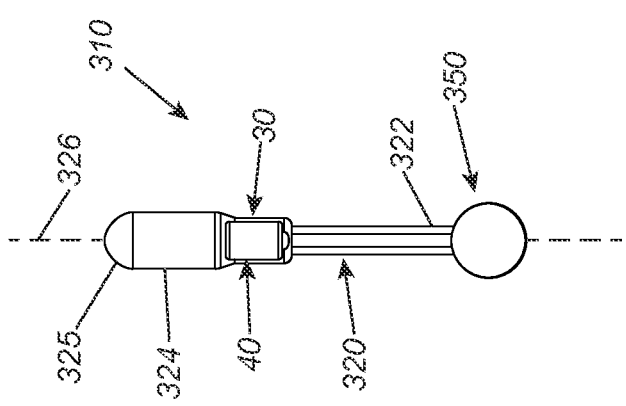

Turning to the drawings, FIGS. 1A-1D show an exemplary embodiment of a guide device 10 to facilitate self-catheterization of a urethra by a female user, e.g., as shown in FIGS. 2A and 2B. Generally, the device 10 includes an elongate anchor member or shaft 20 including a proximal portion 22, a distal portion 24 sized and/or shaped to facilitate insertion into the user's vagina, a bridge 30 extending laterally from an intermediate location of the anchor member 20, a guide 40 on the bridge 30 spaced apart from the anchor member 20, and a handle 50 on the proximal end 22 of the anchor member 20.

The components of the guide device 10 (as well as other devices described herein) may be formed from substantially rigid biocompatible material, e.g., metal, plastic, composite materials, and the like. The material may be sufficiently durable such that the device 10 may use, cleaned, and used again, e.g., multiple times by a user, although alternatively, the device 10 may be a single-use, disposable device, if desired. The components of the device 10 may be formed as an integral unit, e.g., by molding, casting, 3-D printing, or otherwise forming all of the components together. Alternatively, one or more of the components may be formed separately and substantially permanently attached or otherwise assembled together, e.g., by one or more of bonding with adhesive, interference fit, fusing, welding, using one or more fasteners, and the like. For example, the anchor member 10 may be formed separately, and the bridge 20 and handle 50 may be attached to the desired locations on the anchor member 10, as shown and described elsewhere herein.

In the embodiment shown in FIGS. 1A-1C, the anchor member 20 is substantially straight between the proximal and distal portions 22, 24, thereby defining a longitudinal axis 26. In addition, as shown, the anchor member 20 has a substantially uniform cylindrical shape at least along the distal portion 24, e.g., terminating in a distal tip 25. The distal tip 25 may include a rounded, tapered, or other shape to facilitate insertion into a user's vagina with minimal discomfort. The proximal portion 22 may have a tapered cylindrical shape, e.g., extending from the bridge 20 to the handle 50 or, alternatively, may have a substantially uniform diameter (not shown), similar to the devices 110-110" shown in FIGS. 3A-5D. Alternatively, the anchor member 20 may have other shapes, e.g., a cylindrical shape that changes diameter between the proximal and distal portions 22, 24 and/or includes different regions having different substantially uniform diameters (not shown), such as any of the embodiments shown in the applications incorporated by reference herein. For example, the distal portion 24 may have a different size than the proximal portion 22, e.g., with the distal portion defining a substantially uniform diameter that is larger than the diameter of the proximal portion, similar to the device 310 shown in FIGS. 7A-7D. Providing a relatively larger diameter on the distal portion may stabilize the device when the distal portion is inserted into a vagina and/or may facilitate manipulation from the proximal portion, as described elsewhere herein.

As best seen in FIGS. 1A and 1D, the bridge 30 may include a tubular segment 32 sized to fit around the anchor member 20, e.g., such that the tubular segment 32 may be inserted over the distal portion 24 and positioned at a desired location, e.g., at an intermediate location midway along the length of the anchor member 20. In addition, the bridge 30 includes a leg 34 that extends from the tubular segment 32 to support the guide 40. The tubular segment 32 may be permanently or removably mounted at the intermediate location, e.g., by one or more of interference fit, bonding with adhesive, fusing, welding, one or more fasteners, and the like. Alternatively, a curved saddle or other base (not shown) may be provided instead of the tubular segment that may be attached or mounted to the anchor member 20 to secure and support the leg 34. In a further alternative, the leg 34 may be mounted directly to or formed integrally with the anchor member 20 without the tubular segment or other base.

The bridge 30 may be located at any desired distance from the distal tip 25 of the anchor member 20, e.g., to position the guide 40 adjacent the user's urethra but spaced apart sufficiently from the distal tip 25 to facilitate introduction of a urinary catheter into the urethra, as described further elsewhere herein. For example, the bridge 30 may be located and shaped so as to follow the curvature of the anatomy between the user's vagina and urethra. Alternatively, the bridge 30 may be positioned such that the guide 40 is spaced apart a desired distance from the body surface. The leg 34 may extend laterally from the anchor member 20, e.g., along a bridge axis 36 oriented substantially perpendicular to the longitudinal axis 26 of the anchor member 20 and/or otherwise oriented to position the leg 34 flush with the user's skin when the distal portion 24 of the anchor member 20 is fully inserted.

With continued reference to FIGS. 1A and 1B, the guide 40 includes a tubular body including a proximal end 42 and a distal end 44, thereby defining a length therebetween. The guide 40 is mounted or otherwise fixed to the leg 34 of the bridge 30, e.g., such the leg 34 is located at an intermediate location between the proximal and distal ends 42, 44. The guide 40 includes a passage 48 extending between the proximal and distal ends 42, 44 along axis 48, which is sized to receive a urinary catheter 90 therethrough, e.g., as shown in FIG. 2B. In the embodiment shown, the guide 40 is attached to the leg 34 such that the passage 48 (and axis 46) is aligned substantially parallel to the longitudinal axis 26 of the anchor member 20. The guide 40 may be substantially permanently or removably mounted to the leg 34 of the bridge 30 or may be integrated to the leg 34, e.g., using similar methods as used other components described herein.

As shown in FIGS. 1A and 1B, the guide 40 is a straight tubular segment that is shorter than the anchor member 20 and defines a guide axis 46 that extends substantially parallel to the longitudinal axis 26. Consequently, as shown in FIGS. 2A and 2B, a urinary catheter 90 may be inserted into the passage 48 from the proximal end 42 out the distal end 44 directly adjacent the user's urethra 92 to facilitate insertion into the urethra 92. Alternatively, the guide axis may be offset from the longitudinal axis 26, if desired to direct a urinary catheter at an angle relative to the longitudinal axis of the anchor member, e.g., such that the guide axis defines an acute angle that intersects the longitudinal axis, e.g., to direct a catheter anteriorly when the anchor member is inserted into the vagina.

The lateral distance (e.g., distance "L" shown in FIG. 1B) between the anchor member 20 and the guide 40 and/or other dimensions of the device 10 may be selected in advance based on an individual user's anatomy. For example, different devices may be available with each device having a different distance L between the longitudinal axis 26 of the anchor member 20 and the guide axis 46 of the guide 40, e.g., between about four and six millimeters (4-6 mm) to accommodate different individual user's anatomy. A device 10 having desired dimensions may be provided to the user, e.g., after consultation with their medical professional, based on the distance from the individual user's vagina to the user's urethra and/or other anatomical criteria. Alternatively, custom devices may be made and provided to users based on their individual anatomy. See, e.g., https://www.a-jog.org/article/S0002-9378(18)30829-9/fulltext, the entire disclosure of which is expressly incorporated by reference herein, which may provide additional information related to typical anatomical distances and corresponding device dimensions that may be used.

With continued reference to FIGS. 1A-1D, the handle 50 on the proximal end 22 of the anchor member 20 may extend laterally relative to the longitudinal axis 26, which may facilitate a user holding the handle 50 to manipulate the device 10. In the example shown, the handle 50 extends from the proximal end 22 of the anchor member 20 along a handle axis 56 extending laterally relative to the longitudinal axis 26, e.g., substantially perpendicular to the longitudinal axis 26. In addition, as best seen in FIG. 1D, the handle axis 56 may be offset radially relative to the bridge axis 36, e.g., offset substantially ninety degrees relative to the bridge axis 36, to facilitate holding the handle 50 to insert the anchor member 20 and align the guide 40 with the user's urethra. Optionally, the handle 50 may be offset to the right or to the left relative to the bridge 30 and guide 40, e.g., to provide a device for right or left handed users.

Turning to FIGS. 2A and 2B, the device 10 of FIGS. 1A-1D (or any other alternatives described herein) may be used to facilitate self-catheterization by a female user. Initially, as shown in FIG. 2A, the distal portion 24 of the anchor member 20 may be inserted into the user's vagina 94, and then the guide 40 may be aligned with the user's urethra 92. For example, as shown in FIG. 2A, the distal portion 24 may be inserted until the distal end 44 of the guide 40 is positioned against or immediately adjacent the entrance to the urethra 92. It will be appreciated that offsetting the handle 50 relative to the guide 40 may facilitate manipulation of the device 10 and/or insertion of the catheter 90. For example, offsetting the handle 50 to the side of the user's body rather than in line with the path of catheter insertion may allow for precise alignment of the guide 40 with the urethra, reduced obstruction of the path of insertion and/or greater stabilization of the device 10 during subsequent insertion of a urinary catheter.

As shown in FIG. 2B, once the guide 40 is properly aligned, a urinary catheter 90 may be inserted through the passage 48 of the guide 40 into the urethra 92, and then advanced into the user's bladder 96. The user may then void urine from the bladder, whereupon the catheter and anchor member may then be removed, e.g., sequentially or simultaneously, as desired. The catheter 90 may be discarded and the distal portion 24 may be removed. The guide device 10 may be cleaned and reused subsequently, if desired, or also discarded.

Turning to FIGS. 3A-3D, another example of a guide device 110 is shown that includes an elongate anchor member or shaft 120 including a proximal portion 122, a distal portion 124 sized and/or shaped to facilitate insertion into the user's vagina, a bridge 30 extending laterally from the anchor member 120 and a guide 40 on the bridge 30, generally similar to device 10. Unlike the device 10, the anchor member 120 includes a substantially uniform diameter from the proximal portion 122, through the distal portion 124 to a rounded distal tip 125. The proximal portion 122 may have sufficient length proximal to the bride 30 and guide 40 such that the proximal portion 122 may provide a handle to manipulate the device 110 during use. Optionally, the proximal portion 122 may include one or more features to facilitate holding the device 110, e.g., non-slip ridges 128, and the like. In addition or alternatively, if desired, the proximal and distal portions 122, 124 may have different diameters and/or may have variable diameters along their lengths (not shown).

The bridge 30 and guide 40 may be formed with and/or attached to the anchor member 120 similar to other embodiments herein. Consequently, the guide axis 46 and passage 48 through the guide 40 may be aligned substantially parallel to the longitudinal axis 126 of the anchor member 120, which may allow the device 110 to be used similar to other embodiments herein. Alternatively, other bridges and/or guides may be provided on the device 110 (or any of the other guide devices herein).

For example, turning to FIGS. 4A-4D, a guide device 110' is shown that includes an anchor member 120 similar to device 110. The device 110' includes a bridge 130' including a leg 134' coupled between a tubular segment 132' on the anchor member 120 and a guide 140' generally similar to other guide devices herein. However, in this embodiment, the guide 140' includes a curved tubular body including a proximal end 142,' a distal end 144,' and a curved passage 148' extending between the proximal and distal ends 142,' 144' along guide axis 148,' which is sized to receive a urinary catheter (not shown). As shown, at the distal end 144' of the guide 140,' the guide axis 148' may be aligned substantially parallel to the longitudinal axis 126 of the anchor member 120, while at the proximal end 142,' the guide axis 148' may extend laterally, e.g., substantially perpendicular to the longitudinal axis 126.

Consequently, when the distal portion 126 of the anchor member 120 inserted into the user's vagina, the proximal end 142' of the guide 140' may be oriented laterally, e.g., such that the user may rotate or otherwise manipulate the device 110' (e.g., holding the proximal portion 122) to orient the inlet of the guide 140' upwardly, which may facilitate insertion of a urinary catheter (not shown) downwardly into the guide 140." The curved tubular segment may guide the catheter inserted into the curved passage 148' out the outlet in the distal 144' into the user's urethra, e.g., substantially parallel to the longitudinal axis 126.

Yet another alternative embodiment of a guide 140" is shown in FIGS. 5A-5D. Generally, the guide device 110'" includes a bridge 130" including a leg 134" coupled between a tubular segment 132" on an anchor member 120 and the guide 140" generally similar to other guide devices herein. However, in this embodiment, the guide 140" includes a concave saddle or proximal portion 142" leading to an enclosed ring 144," e.g., aligned along guide axis 146," which may extend substantially parallel to the longitudinal axis 126 of the anchor member. During use, once the distal portion 124 of the guide member 120 is inserted into the user's vagina, a catheter (not shown) may be inserted through the guide ring 144," which may direct the catheter distally into the user's urethra. The concave portion 142" may deflect and/or otherwise facilitate directing the tip of the catheter into and through the guide ring 144." Otherwise, the device 110" may be used similar to other embodiments herein.

It will be appreciated that other handles may be provided on the guide devices herein. For example, FIGS. 6A-6D shows an example of a guide device 210 that includes an anchor member 220, a bridge 230, and a guide 40, generally similar to other embodiments herein. In this embodiment, the anchor member 220 includes a proximal portion 222 carrying the bridge 230 and a handle 250. The anchor member 220 also includes a distal portion 224 terminating in a rounded distal tip 225, thereby defining a longitudinal axis 226 extending between the proximal and distal portions 222, 224. As shown, the bridge 230 includes a tubular segment 232 and leg 234 carrying the guide 40, which includes a passage 48 extending along a guide axis 46 aligned with the longitudinal axis 26, similar to other embodiments herein.

Unlike previous embodiments, the handle 250 includes a hilt-shaped body extending from the proximal portion 222, e.g., including a first segment 250a extending laterally from the anchor member 220, a second segment 250b extending substantially parallel to the longitudinal axis 226, and a third segment 250c extending laterally from the second segment 250b, e.g., towards the axis 226. In this configuration, the handle 250 may facilitate manipulation of the device 210 during insertion and/or catheterization via the guide 40, with the handle offset from the guide 40 to avoid interference and/or facilitate visualization during catheterization.

Alternatively, as shown in FIGS. 7A-7D, a "T" shaped handle 350 may be provided on a guide device 310, e.g., instead of the hilt-shaped handle of device 210. Generally, the device 310 includes an anchor portion 320 including a proximal portion 322, a distal portion 324, and carrying a bridge 30 and guide 40, similar to other embodiments. In this embodiment, the distal portion 324 has a substantially uniform diameter that is larger than a cross-section of the proximal portion 322.

Unlike the previous embodiments, a "T" shaped handle 350 is provided on the proximal portion 350 of the anchor member 320 that includes two opposing arms 352 extending laterally from the proximal end 322, e.g., substantially perpendicular to longitudinal axis 326 of the device 310, thereby defining a handle axis 356. As shown, the handle axis 356 may lie within the same plane as the bridge and guide axes 36, 46, although alternatively, the handle axis 356 may be offset radially around the longitudinal axis 226 relative to the bridge axis 36, e.g., ninety degrees, as desired. The "T" shaped handle 350 may facilitate use by both right and left handed users, since the user can hold either arm 352 to manipulate the device 310.

Turning to FIGS. 8A-8C, another example of a guide device 410 is shown that uses the user's pubic bone to facilitate placement and anchoring of the device 410 during self-catheterization. As shown, the guide device 410 includes an elongate anchor member or body 420 including a proximal portion 422 including a handle 450, and a curved distal portion 424 including a guide passage 448, e.g., extending between front and rear surfaces 427, 429 of the elongate body 420. The passage 448 may be spaced a predetermined distance from a distal tip 425 of the distal portion 424, e.g., based on the user's particular anatomy, to facilitate positioning the passage 448 adjacent the user's urethra, as described further below.

In the embodiment shown, the elongate body 420 is formed as a planar sheet having a width "w", e.g., between about forty five and sixty five millimeters (45-65 mm), and a thickness "t", e.g., between about three and ten millimeters (3.0-10 mm), formed from biocompatible materials, e.g., using similar materials and methods as other embodiments herein. The elongate body 420 may have a substantially uniform width "w" and/or thickness "t" along its entire length, e.g., as shown. Alternatively, at least the width of the elongate body 420 may vary, e.g., tapering along the distal portion or transitioning from a wider proximal portion to a narrower distal portion (not shown).

As shown, the distal portion 424 curves relative to the proximal portion 422 such that the front surface 427 has a concave shape along the distal portion 424. For example, the proximal portion 422 may have a slight curvature, e.g., defining a radius of curvature that is larger than the distal portion 424, and the distal portion 424 may define a smaller radius of curvature such that the front surface along the distal portion 424 is concave. Alternatively, the proximal portion 422 may be substantially flat (not shown), and the distal portion 424 may have a uniform or variable radius of curvature defining a concave contact surface extending from the proximal portion to the distal tip. Alternatively, an intermediate region of the elongate body between the proximal and distal portions may have a relatively small radius of curvature, and the proximal and distal portions may have relatively larger radiuses of curvature or may be substantially flat. In this manner, a desired length of the distal portion 424 from the distal tip 425 may be placed securely against the user's pubic bone area to stabilize and position the device 410, as described further below.

In an exemplary embodiment, the elongate body 420, handle 450, and passage 448 may be integrally formed from rigid plastic, e.g., by molding, casting, and the like. Alternatively, the handle 450 may be formed separately and permanently attached to the proximal end 422 and/or the passage 448 may be formed after forming the elongate body 420, e.g., by drilling, stamping, laser cutting, and the like.

As shown, the handle 450 includes two ends 452 attached to the rear surface 429 on the proximal portion 422 and a handle bar 454 extending between the two ends 452 such that the handle bar 454 is spaced away from and extends substantially parallel to the rear surface 429, which may facilitate gripping the handle 450 and/or manipulating the device 410 during use. Alternatively, other handles may be provided on the proximal portion 422, e.g., similar to the handles described elsewhere herein and/or in the applications incorporated by reference herein.

During use, the user may hold the handle 450 and position the distal tip 425 below their pubic bone with the front, i.e., concave, surface 427 oriented towards their body. The distal portion 424 adjacent the distal tip 425 may then be engaged firmly against the pubic bone area with the front surface 427 immediately adjacent their body, thereby stabilizing the device 410 and positioning the passage 448 adjacent their urethra. Similar to other embodiments herein, the user may then insert a urinary catheter (not shown) through the passage 448 into the urethra and advance the catheter into their bladder to void urine. Once completed, the catheter and then device 410 may be removed.

It will be appreciated that a variety of devices 410 may be provided, e.g., having different dimensions, e.g., different distances from the distal tip 425 to the passage 448 and/or different radiuses of curvature and/or widths along the distal portion 424. Thus, the user (e.g., in consultation with their medical professional) may select a device 410 having appropriate dimensions based on their particular anatomy to facilitate self-catheterization. Alternatively, a custom device may be formed for each user based on their individual anatomy. In a further alternative, at least the distal portion 424 of the elongate body 420 may be malleable such that the user may adjust the shape of the distal portion 424, e.g., during their first use to adjust the shape based on their anatomy and then the distal portion 424 may retain the adjusted shape for subsequent use.

Turning to FIGS. 9A-9D, another embodiment of a guide device 510 is shown that generally includes an elongate member or body 520 including a proximal portion 522, and a distal portion 524 carrying an anchor member 540 on or adjacent a distal tip 525. In addition, the elongate member 520 includes a guide passage 548 extending through the distal portion 424 spaced apart from the anchor member 540. As shown, the anchor member 540 extends laterally from the distal portion 524, e.g., such that anchor member 540 defines a guide axis 546 that defines an acute angle relative to a longitudinal axis 526 of the elongate member 520, as shown in FIGS. 9A and 9B. Optionally, the device 510 may include one or more anchor members (not shown) spaced apart from the anchor member 540 along the distal portion 524, e.g., such that the device 510 may be secured at multiple locations relative to the user's body, as described further below.

Similar to other embodiments herein, the passage 548 may be sized to slidably receive a urinary catheter (not shown) therethrough, e.g., substantially parallel or otherwise oriented relative to the guide axis 546, such that the catheter may be inserted into the user's urethra (also not shown). As shown, a handle 550 may be provided that is an extension of the proximal portion 522, e.g., including one or more ridges or other features 552 to facilitate holding and/or manipulating the device 510 during use. Alternatively, other handles may be provided on the proximal portion, e.g., similar to other embodiments described herein.

During use, while holding the handle 550, the user may insert the anchor member 540 into their vagina and position the passage 548 adjacent their urethra. For example, the proximal portion 522 and handle 550 may be sufficiently long that the user orient the handle 550 towards their waist with the anchor member 540 inserted into the vagina. This configuration may facilitate properly orienting the passage 548 for self-catheterization without the user having to bend over, e.g., using tactile feedback without requiring direct visualization. Alternatively, one or more additional anchoring elements may be provided on the distal portion, which may be engaged and/or aligned with other well-known anatomical landmarks, e.g., their clitoris, public bone, and the like, which may facilitate stabilization and/or positioning of the device 510. In this alternative, the passage 548 may be located between two anchor members, e.g., separated by predetermined distances to position the passage 548 adjacent the user's urethra. Similar to other embodiments herein, the user may then insert a urinary catheter (not shown) through the passage 548 into the urethra and advance the catheter into their bladder to void urine. Once completed, the catheter and then device 510 may be removed.

Additional information regarding variations of the devices and methods herein may be found in the applications incorporated by reference herein. It will be appreciated that any combination of the components described herein may be provided and used in combination with one another for the devices and methods herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A device to facilitate self-catheterization of a urethra, comprising:
    an elongate anchor member comprising a proximal portion terminating at a proximal end, a distal portion sized and/or shaped to facilitate insertion into a user's vagina, and a longitudinal axis extending between the proximal and distal portions, the distal portion having a cylindrical shape terminating in a rounded or tapered distal tip;
    a bridge extending laterally from an intermediate location of the anchor member along a bridge axis between the proximal and distal portions;
    a guide on the bridge spaced apart from the anchor member, the guide comprising a tubular member having a length shorter than a length of the anchor member and including a passage therethrough sized to receive a urinary catheter therethrough; and
    a handle permanently attached to and extending from the proximal end of the anchor member along a handle axis substantially perpendicular and fixed permanently relative to the longitudinal axis,
    wherein the longitudinal axis and the handle axis lie within a plane and the bridge axis extends out of the plane such that the handle is out of a path of catheter insertion when a urinary catheter is inserted through the guide into a urethra to reduce obstruction of the path of insertion.

2. The device of claim 1, wherein the anchor member has a substantially uniform diameter between the proximal and distal portions.

3. The device of claim 1, wherein the distal portion has a cross-section larger than a cross-section of the proximal portion.

4. The device of claim 1, wherein the tubular member defines a guide axis that is aligned substantially parallel to the longitudinal axis.

5. The device of claim 4, wherein the tubular member is substantially straight.

6. The device of claim 1, wherein the bridge axis is substantially perpendicular and fixed permanently relative to the longitudinal axis.

7. The device of claim 6, wherein the handle axis is offset substantially ninety degrees around the longitudinal axis relative to the bridge axis when viewed from the proximal end of the anchor member.

8. The device of claim 6, wherein the handle has a hilt-shape.

9. The device of claim 1, wherein the handle comprises a "T" shaped handle including opposite arms extending from the proximal end along the handle axis.

10. The device of claim 1, wherein the anchor member is substantially rigid.

11. A method for self-catheterization by a user, comprising:
providing a guide device comprising an elongate anchor member defining a longitudinal axis between proximal and distal portions thereof, the proximal portion terminating at a proximal end, a bridge extending laterally from an intermediate location of the anchor member along a bridge axis, a guide comprising a tubular member on the bridge and spaced apart from the anchor member and including a passage extending substantially parallel to the longitudinal axis, and a handle permanently attached to and extending from the proximal portion of the anchor member along a handle axis substantially perpendicular and fixed permanently relative to the longitudinal axis, the handle axis and offset relative to the bridge axis around the longitudinal axis when viewed from the proximal end of the anchor member;
while holding the handle, inserting the distal portion of the anchor member into the user's vagina to align the guide with the user's urethra;
inserting a urinary catheter through the passage of the guide into the urethra;
advancing the catheter into the user's bladder;
voiding urine from the bladder; and
removing the catheter and anchor member.

12. The method of claim 11, further comprising orienting the handle substantially horizontally to orient the guide substantially vertically relative to the anchor member to align the passage with the user's urethra before inserting the urinary catheter through the passage of the guide into the urethra.

13. The method of claim 11, further comprising holding the handle while inserting the urinary catheter, wherein the handle axis is offset from the bridge axis such that the handle is out of a path of catheter insertion when the urinary catheter is inserted through the guide into the urethra to reduce obstruction of the path of insertion.

14. A device to facilitate self-catheterization of a urethra, comprising:
an elongate anchor member comprising a proximal portion, a distal portion sized and/or shaped to facilitate insertion into a user's vagina, and a longitudinal axis extending between the proximal and distal portions, the distal portion having a cylindrical shape terminating in a rounded or tapered distal tip;
a bridge extending from an intermediate location of the anchor member between the proximal and distal portions, the bridge extending along a bridge axis extending substantially perpendicular and fixed permanently relative to the longitudinal axis;
a tubular guide on the bridge spaced apart from the anchor member, the guide comprising a passage therethrough aligned with the longitudinal axis and sized to receive a urinary catheter therethrough; and
a handle permanently attached to and extending from the proximal portion of the anchor member along a handle axis extending substantially perpendicular and fixed permanently relative to the longitudinal axis, the handle axis offset from the bridge axis around the longitudinal axis when viewed from the proximal end of the anchor member such that the handle is out of a path of catheter insertion when the urinary catheter is inserted through the guide into the urethra to reduce obstruction of the path of insertion.

15. The device of claim 14, wherein the handle axis is offset around the longitudinal axis substantially ninety degrees relative to the bridge axis.

16. The device of claim 14, wherein the intermediate location is midway along a length of the anchor member.

17. The device of claim 14, wherein the proximal portion of the anchor member has a cylindrical shape.

18. The device of claim 14, wherein the proximal and distal portions of the anchor member have a cylindrical shape having a substantially uniform diameter between the proximal and distal portions.

* * * * *